United States Patent [19]

Krämer et al.

[11] Patent Number: 4,470,994

[45] Date of Patent: Sep. 11, 1984

[54] ANTIMICROBIAL AGENTS AND THEIR USE

[75] Inventors: Wolfgang Krämer, Wuppertal; Karl H. Büchel, Burscheid; Hans-Ludwig Elbe, Wuppertal; Udo Kraatz, Leverkusen; Wolf Reiser; Erik Regel, both of Wuppertal; Andreas Schulze, Berg.-Gladbach; Manfred Plempel, Wuppertal, all of Fed. Rep. of Germany

[73] Assignee: Bayer Aktiengesellschaft, Leverkusen, Fed. Rep. of Germany

[21] Appl. No.: 343,053

[22] Filed: Jan. 27, 1982

[30] Foreign Application Priority Data

Feb. 7, 1981 [DE] Fed. Rep. of Germany ....... 3104380

[51] Int. Cl.$^3$ ................. A61K 31/415; A61K 31/495; A61K 31/41

[52] U.S. Cl. ................. 424/273 R; 424/250; 424/269

[58] Field of Search ............ 424/269, 273 R

[56] References Cited

U.S. PATENT DOCUMENTS 4,156,008  5/1979  Heeres .................. 424/273 R
4,329,342  5/1982  Heeres et al. ........... 424/245

FOREIGN PATENT DOCUMENTS 2943631  5/1980  Fed. Rep. of Germany.

Primary Examiner—Albert T. Meyers
Assistant Examiner—John W. Rollins, Jr.
Attorney, Agent, or Firm—Sprung, Horn, Kramer & Woods

[57] ABSTRACT

The invention relates to pharmaceutical compositions containing an active antimicrobial compound of Formula (I). Also included in the invention are methods for combatting mycoses utilizing the above-identified pharmaceutical composition.

17 Claims, No Drawings

ANTIMICROBIAL AGENTS AND THEIR USE

The present invention relates to the use as antimicrobial agents of certain 2-azolylmethyl-1,3-dioxolane and -dioxane derivatives which are novel.

It has already been disclosed that 2-(2,4-dichlorophenyl)-2-(imidazol-1-yl-methyl)-1,3-dioxolane derivatives, such as 4-(4-biphenylyloxymethyl)-2-(2,4-dichlorophenyl)-2-(imidazol-1-yl-methyl)-1,3-dioxolane and 4-[4-(4'-acetylpiperazine-1-yl)-phenoxymethyl]-2-(2,4-dichlorophenyl)-2-(imidazol-1-yl-methyl)-1,3-dioxolane, have good antimycotic properties (see DE-OS (German Published Specification) No. 2,602,770 and DE-OS (German Published Specification) No. 2,804,096). However, the action of these compounds is not always completely satisfactory.

According to the present invention there is provided a pharmaceutical composition containing as an active ingredient a compound which is a 2-azolyl-methyl-1,3-dioxolane and -dioxane derivatives of the general formula $$R^6-(CH_2)_n-C(CH_3)_2-\underset{O}{C}-\underset{O}{CH_2}-Az \quad (I)$$

$$\begin{array}{c} R^2 \diagdown \diagup R^4 \\ R^1 \quad (CH)_m \quad R^3 \\ | \\ R^5 \end{array}$$

or a pharmaceutically acceptable acid addition salt thereof, in which

Az represents an imidazol-1-yl or 1,2,4-triazol-1-yl radical, $R^1$, $R^2$ and $R^3$ independently represent a hydrogen atom or an alkyl radical, $R^4$ represents a hydrogen atom or an optionally substituted alkyl, optionally substituted aryl or optionally substituted aralkyl radical, or $R^1$ and $R^3$ additionally represent an optionally substituted multi-membered methylene bridge, $R^5$ represents a hydrogen atom or an alkyl radical, m is 0 or 1, $R^6$ represents a hydrogen or halogen atom, a cyano, alkyl or optionally substituted aryl radical or a grouping of the general formula $$-X-R^7, -COOR^8 \text{ or } -CONHR^9,$$

in which

X represents an oxygen or sulphur atom or an SO— or SO$_2$— group, $R^7$ represents an alkyl, halogenoalkyl, cyano, optionally substituted aralkyl or optionally substituted aryl radical, $R^8$ represents an alkyl radical, $R^9$ represents an alkyl radical or an optionally substituted aryl radical, and n is 0 or 1, in admixture with an inert pharmaceutical carrier, e.g. a solid or liquid gaseous diluent, or in admixture with a liquid diluent other than a solvent of a molecular weight less than 200 except in the presence of a surface active agent.

The compositions of the present invention have good antimicrobial, particularly antimycotic, properties.

The compounds of the formula (I) can occur as various stereoisomers, if appropriate; they are preferably produced in the form of stereoisomer mixtures.

The 2-azolylmethyl-1,3-dioxolane and -dioxane derivatives to be used in compositions according to the invention surprisingly show a better antimycotic action, in particular against Microsporum species and Aspergillus species, than the compounds known from the state of the art, namely 4-(4-biphenylyloxymethyl)-2-(2,4-dichlorophenyl)-2-(imidazol-1-yl-methyl)-1,3-dioxolane and 4-[4-(4'-acetylpiperazin-1yl)-phenoxymethyl]-2-(2,4-dichlorophenyl)-2-(imidazol-1-yl-methyl)-1,3-dioxolane, which are related compounds chemically and in terms of their action. The use, according to the invention, of the new substances thus represents an enrichment of medicine.

Formula (I) gives a general definition of the 2- azolyl-methyl-1,3-dioxolane and -dioxane derivatives to be used according to the invention.

Preferred compounds of the formula (I) for use in compositions of the present invention are those in which $R^1$, $R^2$ and $R^3$ independently represent a hydrogen atom or a straight-chain or branched alkyl radical having 1 to 4 carbon atoms;

$R^4$ represents a hydrogen atom, a straight-chain or branched alkyl radical which has 1 to 4 carbon atoms and which is optionally substituted by hydroxyl, alkoxy having 1 to 4 carbon atoms, dialkylamino and dialkylaminocarbonyl, each having 1 or 2 carbon atoms in each alkyl part, optionally substituted (especially mono-, di- or tri-) phenoxy and optionally (especially mono-, di- or tri-) substituted phenylalkoxy having 1 to 4 carbon atoms in the alkyl part, optionally (especially mono-, di- or tri-) substituted phenylcarboxy and optionally (especially mono-, di- or tri-) substituted phenylalkylcarboxy having 1 to 4 carbon atoms in the alkyl part, alkylsulphonyloxy having 1 to 4 carbon atoms and optionally (especially mono-, di- or tri-) substituted phenylsulphonyloxy (the following being mentioned as preferred suitable phenyl substituents in each case; halogen, alkyl having 1 to 4 carbon atoms, alkoxy and alkylthio, each having 1 or 2 carbon atoms, halogenoalkyl, halogenoalkoxy and halogenoalkylthio, each having 1 or 2 carbon atoms and 1 to 5 identical or different halogen atoms (such as, in particular, fluorine atoms and chlorine atoms), dimethylamino, acetylamino, acetylmethylamino, and piperazine which is optionally substituted by methyl or acetyl); or $R^4$ represents an optionally (especially mono-, di- or tri-) substituted phenyl radical or an optionally (especially mono-, di-, or tri-) substituted phenylalkyl radical having 1 to 4 carbon atoms in the alkyl part, (substituent(s) in both cases preferably being the abovementioned preferred suitable phenyl substituents); or $R^1$ and $R^3$ additionally together represent a tetra- or pentamethylene bridge which is optionally substituted by alkyl having 1 to 4 carbon atoms;

$R^5$ represents a hydrogen atom or a straight-chain or branched alkyl radical having 1 to 4 carbon atoms;

$R^6$ represents a hydrogen or halogen atom, a cyano radical, a straight-chain or branched alkyl radical having 1 to 4 carbon atoms, an optionally substituted phenyl radical (preferably being substituted by the mentioned preferred suitable phenyl substituents of $R^4$), or a grouping of the formula —X—$R^7$, —$COOR^8$ or —$CONHR^9$, in which $R^7$ represents a straight-chain or branched alkyl radical having 1 to 4 carbon atoms, halogenoalkyl having 1 or 2 carbon atoms and 1 to 5 identical or different halogen atoms (such as, in particular, fluorine atoms and chlorine atoms), a cyano radical, an optionally (especially mono-, di- or tri-) substituted phenyl radical or an optionally (especially mono-, di- or tri-) substituted phenylalkyl radical having 1 to 4 carbon atoms in the alkyl part (substituent(s) in both cases preferably being the abovementioned preferred suitable phenyl substituents of $R^4$);

$R^8$ represents a straight-chain or branched alkyl radical having 1 to 4 carbon atoms;

$R^9$ represents a straight-chain or branched alkyl radical having 1 to 4 carbon atoms, or an optionally (especially mono- di-, or tri-) substituted phenyl radical (the phenyl substituent(s) preferably being the abovementioned preferred suitable phenyl substituents of $R^4$);

n represents 1; and

Az, X and m have the abovementioned meanings.

Particularly preferred compounds of the formula (I) for use in the compositions of the present invention are those in which $R^1$, $R^2$ and $R^3$ individually have the same meanings as in the above preferred compounds used according to the invention;

$R^4$ represents a hydrogen atom, or a straight-chain or branched alkyl radical which has 1 to 4 carbon atoms and which is optionally substituted by hydroxyl, methoxy, ethoxy, dimethylamino, dimethylaminocarbonyl, optionally (especially mono-, di- or tri-) substituted phenoxy and benzyloxy, methylcarboxy, ethylcarboxy, optionally substituted phenylcarboxy and benzylcarboxy, methylsulphonyloxy, ethylsulphonyloxy or optionally (especially mono-, di- or tri-) substituted phenylsulphonyloxy (the following being mentioned as phenyl substituents in each case: fluorine, chloride, methyl, ethyl, methoxy, methylthio, trifluoromethyl and trifluoromethylthio, dimethylamino, acetylamino, acetyl-methylamino, 4-acetyl-piperazin-1-yl, nitro, methylcarboxy and ethylcarboxy); or $R^4$ represents an optionally substituted phenyl or benzyl radical (the immediately abovementioned phenyl substituents being suitable phenyl substituents);

$R^1$ and $R^3$ additionally together can represent a tetramethylene bridge;

$R^5$ represents a hydrogen atom or a methyl or ethyl radical;

$R^6$ represents a hydrogen, fluorine, chlorine or bromine atom or a methyl, ethyl, propyl or optionally substituted phenyl radical (the phenyl substituents already mentioned immediately above in the case of $R^4$ being suitable substituents) or a grouping of the formula —X—$R^7$, —$COOR^8$ or —$CONHR^9$, in which $R^7$ represents a methyl, ethyl, trifluoromethyl or cyano radical, or an optionally substituted phenyl or benzyl radical (the phenyl substituents already mentioned immediately above in the case of $R^4$ being suitable phenyl substituents in each case)

$R^8$ represents a methyl or ethyl radical;

$R^9$ represents a methyl or ethyl radical or an optionally (especially mono-, di- or tri-) substituted phenyl radical, the phenyl substituents already mentioned immediately above in the case of $R^4$ being suitable phenyl substituents);

n is 1: and

Az, X and m have the abovementioned meanings.

The active compounds to be used according to the invention are novel. However, they can be prepared, according to a proposal of the applicants, by a process in which (a) a substituted 1,3-dioxolane and -dioxane derivative of the formula

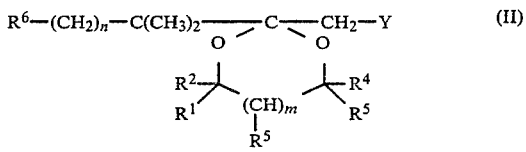

in which $R^1$ to $R^6$, m and n have the meanings given above, and

Y represents a halogen atom (preferably a chlorine or bromine atom) or a grouping of the formula —O—$SO_2$—Z, wherein Z represents a methyl or p-methylphenyl radical, is reacted with an alkali metal salt of an azole of the formula

M—AZ (III)

in which

Az have the meaning given above and

M represents an alkali metal, in the presence of an inert organic solvent (such as dimethylformamide) at a temperature between 60° and 150° C., or (b) an azolylmethyl-keto derivative of the formula

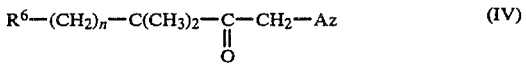

in which

Az, $R^6$ and n have the meanings given above, is reacted with a diol of the formula

in which $R^1$ to $R^5$ and m have the meanings given above, in the presence of an inert organic solvent (such as toluene) and in the presence of a strong acid as a catalyst (such as p-toluenesulphonic acid) at a temperature between 80° and 100° C., if appropriate under elevated pressure.

If desired, an acid can subsequently be added on to the compounds of the formula (I) thus obtained to give the acid addition salt thereof. In some cases it proves to be advantageous to obtain the compounds of the formula (I) in pure form via their salts.

The substituted 1,3-dioxolane and -dioxane derivatives of the formula (II) are novel. They are obtained by a process in which a keto derivative of the formula

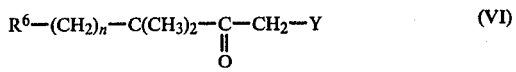

$$R^6-(CH_2)_n-C(CH_3)_2-\underset{O}{\overset{\|}{C}}-CH_2-Y \qquad (VI)$$

in which

Y, $R^6$ and n have the meaning given above, is reacted with a diol of the formula (V) according to the conditions of reaction variant (b).

Some of the keto derivatives of the formula (VI) are known (see DE-OS (German Published Specification) No. 2,635,663), and some of them are the subjects of our, as yet unpublished, prior applications corresponding, respectively, to German patent application Nos. P 30 21 551 of 7.6.1980 and P 30 48 266.7 of 20.12.1980. They are obtained, for example, by reacting the appropriate ketones with chlorine or bromine in the presence of an inert organic solvent (such as ether, or a chlorinated or non-chlorinated hydrocarbon) at room temperature, or with customary chlorinating agents (such as sulphuryl chloride) at 20° to 60° C.

The alkali metal salts of azoles of the formula (III) are generally known. They are obtained by the reaction of imidazole or 1,2,4-triazole with sodium methylate or potassium methylate, or by the reaction of imidazole or triazole with the equivalent quantity of the corresponding alkali metal hydride.

Some of the azolylmethyl-keto derivatives of the formula (IV) are known (see, for example, DE-OS (German Published Specification) 2,431,407 and DE-OS (German Published Specification) 2,906,061), and some of them are the subjects of our, as yet unpublished, prior applications corresponding, respectively, to German patent application Nos. P 30 28 330 of 25.7.1980 and P 30 48 266.7 of 20.12.1980.

They are obtained by reacting a keto derivative of the formula (VI) with an alkali metal salt of an azole of the formula (III) according to the conditions of reaction variant (a), or directly with an azole, in the customary manner, in the presence of an acid-binding agent.

The diols of the formula (V) are generally known compounds of organic chemistry, or are obtained in a generally known manner.

The following are preferred suitable acids for the preparation of pharmaceutically acceptable acid addition salts of the compounds of the formula (I): hydrogen halide acids (such as hydrobromic acid and, preferably hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid) or a sulphonic acid (such as p-toluenesulphonic acid or 1,5-naphthalenedisulphonic acid). The acid addition salts of the compounds of the formula (I) can be obtained in a simple manner by customary methods of salt formation, for example by dissolving a compound of the formula (I) in a suitable inert solvent and adding the acid, for example hydrochloric acid, and can be isolated in a known manner, for example by filtering off, and can be purified, if required, by washing with an inert organic solvent.

The compounds of the formula (I) which can be used according to the invention, and their acid addition salts, display antimicrobial action, in particular powerful antimycotic action. They possess a very broad antimycotic action spectrum, especially against dermatophytes and blastomyces as well as biphase fungi, for example against varieties of Candida, such as Candida albicans, varieties of Epidermophyton, such as Epidermophyton floccosum, varieties of Aspergillus, such as Aspergillus niger and Aspergillus fumigatus, varieties of Trichophyton, such as Trichophyton mentagrophytes, varieties of Microsporon, such as Microsporon felineum and varieties of Penicillium, such as Penicillium commune. The listing of these micro-organisms in no way implies a limitation of the germs which can be combated but is only illustrative.

Examples which may be mentioned of fields of indication in medicine are: dermatomycoses and systemic mycoses caused by Trichophyton mentagrophytes and other varieties of Trichophyton, varieties of Microsporon, Epidermophyton floccosum, blastomyces and biphase fungi as well as moulds.

As stated above, the invention also relates to the use in medicine of the compounds of the invention.

The present invention provides a pharmaceutical composition containing as active ingredient a compound of the invention in admixture with an inert pharmaceutical carrier, e.g. a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5%, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 2.5 g to 10 g of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably parenterally, especially intravenously. Preferred pharmaceutical compositions and medicaments are therefore those adapted for administration such as parenteral administration. Administration in the method of the invention is preferably parenteral administration.

In general it has proved advantageous to administer amounts of from 10 to 300 mg/kg, preferably 50 to 200 mg/kg of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples 1 to 66 illustrate processes for the production of compounds used in the present invention.

EXAMPLE 1

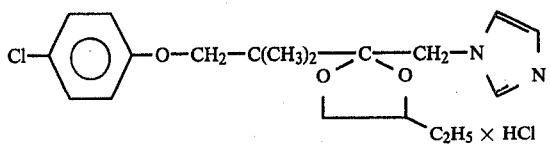

(Reaction variant (a))

25.8 g ($3.8\times10^{-1}$ mol) of imidazole were dissolved in 600 ml of dimethylformamide, 20.5 g ($3.8\times10^{-1}$ mol) of sodium methylate, dissolved in 60 ml of methanol, were added dropwise to the solution and the methanol was distilled off. 74 g ($1.9\times10^{-1}$ mol) of crude 2-bromomethyl-2-[β-(4-chlorophenoxy)-α,α-dimethyl]-ethyl-4-ethyl-1,3-dioxolane (content 62%, gas chromatography) were added dropwise to the mixture at 80° C., and the mixture was heated under reflux for a further 6 hours. After the mixture has been cooled, it is stirred into 2 liters of water and extracted with twice 500 ml of toluene, and the combined toluene phases were extracted with three times 250 ml of water and the solvent was distilled off in a water jet vacuum. The residue was taken up in 300 ml of diisopropyl ether and saturated ethereal hydrochloric acid was added to the solution. The resulting precipitate was filtered off under suction. 39.7 g (84% of theory) of 2-(imidazol-1-yl)-methyl-2-[β-(4-chlorophenoxy)-α,α-dimethyl]-ethyl-4-ethyl-1,3-dioxolane hydrochloride of melting point 146° to 147° C. were obtained.

Preparation of the starting material

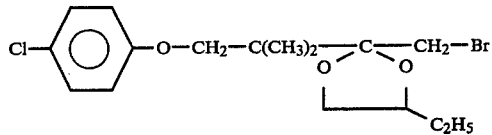

91 g ($3\times10^{-1}$ mol) of 1-bromo-3,3-dimethyl-4-(4-chlorophenoxy)-butan-2-one were dissolved in 400 ml of toluene, 54 g ($6\times10^{-1}$ mol) of 1,2-butanediol and 5.2 g ($3\times10^{-2}$ mol) of p-toluenesulphonic acid were added to the solution, and the reaction mixture was then heated under reflux for 16 hours in a water separator. After the mixture had been cooled, the organic phase was washed with twice 250 ml of saturated sodium bicarbonate solution and the solvent was distilled off in a water jet vacuum. 120 g of crude 2-bromomethyl-2-[β-(4-chlorophenoxy)-α,α-dimethyl]-ethyl-4-ethyl-1,3-dioxolane (gas chromatographic content 62%) were obtained and were directly further reacted.

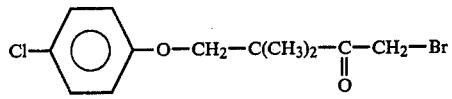

26 g (0.159 mol) of 1-(4-chlorophenoxy)-2,2-dimethyl-butan-3-one were dissolved in 300 ml of chloroform and 25.5 g (0.159 mol) of bromine were added dropwise to the solution, at 20° C., at such a rate that decolorisation occurred continuously. After the end of the addition, the mixture was stirred for 30 minutes at room temperature and was then concentrated by distilling off the solvent in vacuo. 48.5 g of 1-bromo-4-(4-chlorophenoxy)-3,3-dimethylbutan-2-one of boiling point 150°–160° C./0.14 mm Hg were obtained (quantitative conversion).

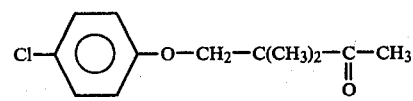

29.7 g (0.55 mol) of sodium methylate were dissolved in 500 ml of methanol and 70.4 g (0.55 mol) of 4-chlorophenol were added to the solution, whilst stirring. After the mixture had been stirred for 10 minutes, the solvent was distilled off under reduced pressure and the residue was taken up in 100 ml of glycol. This solution was added to a solution of 135 g (0.5 mol) of 2,2-dimethyl-1-tosyloxy-butan-3-one in 200 ml of glycol. The reaction mixture was stirred for 48 hours at 100° to 120° C., and was cooled and stirred into 2,000 ml of water. The mixture was extracted with twice 250 ml of diethyl ether, and the combined organic phases were washed with three times 100 ml of water, once with 100 ml of 10% strength sodium hydroxide solution and again with 100 ml of water, dried over sodium sulphate and distilled. 62.9 g (55.7% of theory) of 1-(4-chlorophenoxy)-2,2-dimethylbutan-3-one of boiling point 135°–140° C./0.4 mm Hg were obtained.

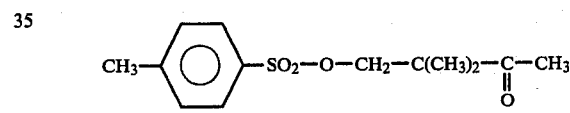

47.6 g (0.25 mol) of 4-toluenesulphonyl chloride were dissolved in 100 ml of chloroform, 35 g (0.3 mol) of 2,2-dimethyl-1-hydroxybutan-3-one were added to the solution and 40 ml (0.5 mol) of pyridine were added dropwise to the mixture at 0° to 5° C. The reaction mixture was further stirred for 15 hours at room temperature and was discharged onto 200 g of ice and 70 ml of concentrated hydrochloric acid, and the organic phase was separated off, washed with three times 200 ml of water, dried over sodium sulphate and concentrated. The residue was taken up in 100 ml of petroleum ether, the end product crystallising out. 46 g (71% of theory) of 2,2-dimethyl-1-tosyloxy-butan-3-one were obtained as colourless crystals of melting point 49°–52° C.

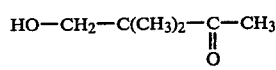

66 g (2.2 mol) of paraformaldehyde and 1 g of potassium hydroxide in 10 ml of methanol were added dropwise to 172 g (2 mol) of methyl isopropyl ketone in 1,000 ml of methanol. The mixture was heated under reflux for 15 hours and the methanol was then distilled off over a column at an internal temperature of 82° C. The residue was distilled in a water jet vacuum. 152.7 g (68% of theory) of 2,2-dimethyl-1-hydroxy-butan-3-one of boiling point 80°–82° C./12 mm Hg were obtained.

EXAMPLE 2

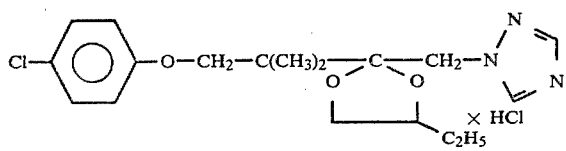

(Reaction variant (a))

16.8 g ($3.1 \times 10^{-1}$ mol) of sodium methylate in 60 ml of methanol were added dropwise to 21.4 g ($3.1 \times 10^{-1}$ mol) of 1,2,4-triazole in 600 ml of dimethylformamide and the methanol was distilled off. 60 g ($1.56 \times 10^{-1}$ mol) of 2-bromomethyl-2-[β-(4-chlorophenoxy)-α,α-dimethyl]-ethyl-4-ethyl-dioxolane (content 62%, gas chromatography) were added dropwise at 80° C., and the reaction mixture was heated under reflux for 15 hours. The cooled dimethylformamide solution was stirred into 2 liters of water and was extracted with twice 250 ml of toluene. The toluene phase was washed with three times 250 ml of water and dried over sodium sulphate, and the solvent was distilled off in a water jet vacuum. 20 g of crude product were obtained, and this product was taken up in 200 ml of diethyl ether and 20 ml of saturated ethereal hydrochloric acid were added to the solution. The solvent was distilled off and the residue was again taken up in 200 ml of ether. An oil was obtained, from which the ethereal phase was decanted off. After chromatography over a silica gel column (250 g of silica gel 60) in chloroform/methanol, 7.8 g (17.4% of theory) of 2-(1,2,4-triazol-1-yl)-methyl-2-[β-(4-chlorophenoxy)-α,α-dimethyl]-ethyl-4-ethyl-1,3-dioxolane hydrochloride of melting point 109° C. were obtained.

The following compounds of the formula

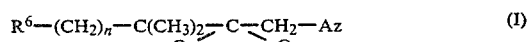

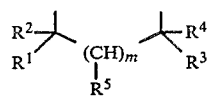

were obtained in a corresponding manner and according to the processes given:

| Example No. | ![structure] | R⁶ | n | Az | Melting point (°C.) |
|---|---|---|---|---|---|
| 3 | dioxolane with C₂H₅ | H | 1 | triazolyl | 220 (× HCl) |
| 4 | dioxolane with C(CH₃)₃ | " | 1 | " | 132 (× HCl) |
| 5 | dioxolane with C₃H₇ | " | 1 | " | 190–92 (× HCl) |
| 6 | " | Cl—C₆H₄—O— | 1 | " | 145 (× HCl) |
| 7 | dioxolane with C₂H₅ | 2,4-Cl₂—C₆H₃—O— | 1 | " | 156 (× HCl) |
| 8 | dioxolane with C₃H₇ | " | 1 | " | 144 (× HCl) |

-continued

| Example No. | (dioxolane structure with R¹-R⁵) | R⁶ | n | Az | Melting point (°C.) |
|---|---|---|---|---|---|
| 9 | dioxolane-C₂H₅ | 2,6-dichloro-methoxyphenyl | 1 | " | 138 (× HCl) |
| 10 | dioxolane fused cyclohexane (H) | 2,4-dichloro-methoxyphenyl | 1 | " | 142 (× HCl) |
| 11 | dioxolane-C₂H₅ | 4-bromo-methoxyphenyl | 1 | " | 174 (× HCl) |
| 12 | dioxolane | 4-chloro-methoxyphenyl | 1 | imidazole | 169 (× HCl) |
| 13 | dioxolane-C₃H₇ | " | 1 | " | viscous oil 153–154 (× HCl) |
| 14 | dioxolane-CH₃ | " | 1 | " | 127 (× HCl) |
| 15 | dioxolane-CH₂OH | " | 1 | " | 148 (× HCl) |
| 16 | dioxolane-CH₃ | 2,4-dichloro-methoxyphenyl | 1 | " | 166 (× HCl) |
| 17 | dioxolane-C₂H₅ | " | 1 | " | 158 (× HCl) |
| 18 | dioxolane-C₃H₇ | " | 1 | " | 154 (× HCl) |

-continued

| Example No. | m with dioxane ring) | R⁶ | n | Az | Melting point (°C.) |
|---|---|---|---|---|---|
| 19 | dioxane-CH-C₂H₅ | 2,6-dichlorophenoxy | 1 | " | 169 (× HCl) |
| 20 | dioxane fused cyclohexane (H) | 2,4-dichlorophenoxy | 1 | " | 135 (× HCl) |
| 21 | dioxane-CH-C₂H₅ | 4-bromophenoxy | 1 | " | 176 (× HCl) |
| 22 | dioxane-CH-C₃H₇ | H | 1 | " | 173 (× HCl) |
| 23 | dioxane-CH-CH₂OH | " | 1 | " | 168 (× HCl) |
| 24 | dioxane fused cyclohexane (H) | " | 1 | " | 222 (× HCl) |
| 25 | dioxane-CH₂-CH-CH₃ | 4-chlorophenoxy | 1 | " | viscous oil |
| 26 | " | " | 1 | " | 162 (× HCl) |
| 27 | dioxane-CH-C₂H₅ | 4-chlorophenylthio | 1 | " | 92 |
| 28 | " | phenylthio | 1 | " | viscous oil |

-continued

| Example No. | ![dioxolane structure with R1-R5] | R⁶ | n | Az | Melting point (°C.) |
|---|---|---|---|---|---|
| 29 | " | " | 1 | 1,2,4-triazol-1-yl | viscous oil |
| 30 | 2,2-dimethyl-4-methyl-1,3-dioxolane | 4-Cl-C₆H₄-S- | 1 | 1,2,4-triazol-1-yl | viscous oil |
| 31 | " | " | 1 | imidazol-1-yl | viscous oil |
| 32 | " | 2,4-diCl-C₆H₃-O- | 1 | 1,2,4-triazol-1-yl | 152 (× HCl) |
| 33 | 2,2-dimethyl-4-ethyl-1,3-dioxolane | 3-CH₃-4-Cl-C₆H₃-O- | 1 | imidazol-1-yl | 170 (× HCl) |
| 34 | 2,2-dimethyl-4-(CH₂OSO₂CH₃)-1,3-dioxolane | 4-Cl-C₆H₄-O- | 1 | 1,2,4-triazol-1-yl | crystal slurry |
| 35 | 2,2-dimethyl-4-ethyl-1,3-dioxolane | 3-CH₃-4-Cl-C₆H₃-O- | 1 | " | 167 (× HCl) |
| 36 | " | 2-Cl-6-CH₃-C₆H₃-O- | 1 | " | 129 (× HCl) |
| 37 | " | " | 1 | imidazol-1-yl | 184 (× HCl) |
| 38 | 2,2-dimethyl-1,3-dioxolane | 4-Cl-C₆H₄-O- | 1 | pyrazol-1-yl | 180–82 (× HCl) |

-continued

| Example No. | $\begin{array}{c} \phantom{xx}O\phantom{-}C\phantom{-}O \\ R^2\phantom{xxxx}R^4 \\ R^1-(CH)_m-R^3 \\ \phantom{xxxx}R^5 \end{array}$ | $R^6$ | n | Az | Melting point (°C.) |
|---|---|---|---|---|---|
| 39 | O-C-O with CH₃ | " | 1 | " | 179–82 (× HCl) |
| 40 | O-C-O | " | 1 | " | crystal slurry (× HCl) |
| 41 | " | H₃C—⌬—O— | 1 | " | $n_D^{20} =$ 1,5142 |
| 42 | O-C-O with C₂H₅ | " | 1 | " | $n_D^{20} =$ 1,5264 |
| 43 | O-C-O | H—⌬—O— with Br | 1 | " | $n_D^{20} =$ 1,5305 |
| 44 | O-C-O with C₂H₅ | CH₃, —O— with Br | 1 | " | $n_D^{20} =$ 1,5283 |
| 45 | " | " | 1 | " | 137 (× ½ NDS)* |
| 46 | " | Cl—⌬—S— | 1 | " | Oil |
| 47 | " | Cl—⌬— | 0 | " | 74 |
| 48 | O-C-O with H₃C, CH₃ | Cl, Cl—⌬—O— | 1 | " | 180 (× HCl) |
| 49 | " | Cl, Cl—⌬—O— | 1 | —N⟨N⟩ | 166–68° C. (× HCl) |

-continued

| | | | | |
|---|---|---|---|---|
| Example No. | (structure with R¹-R⁵ on dioxane ring) | R⁶ | n Az | Melting point (°C.) |
| 50 | (dioxolane, unsubstituted) | " | 1 " | 172° C. (× HCl) |
| 51 | " | " | 1 | (triazole) 157–59° C. (× HCl) |
| 52 | (dioxolane with C₂H₅) | H₃C—C₆H₃(Cl)—O— | 1 | (imidazole) 147–49° C. (× HCl) |
| 53 | " | " | 1 | (triazole) 90° C. (× HCl) |
| 54 | " | CH₃—C₆H₃(Cl)—O— | 1 | (imidazole) 160° C. (× HCl) |
| 55 | (dioxolane with CH₂—O—C₆H₃(Cl)₂) | Cl—C₆H₄—O— | 1 " | 170° C. |
| 56 | (dioxolane with CH₂—N(C₂H₅)₂) | " | 1 " | semi-crystalline |
| 57 | (dioxolane with C₂H₅) | CH₃—C₆H₃(Cl)—O— | 1 | (triazole) 150° C. (× HCl) |
| 58 | " | H₃C, O₂N—C₆H₃—O— | 1 " | 61° C. |

-continued

| Example No. | $\begin{array}{c} R^2\\R^1 \end{array}\overset{\displaystyle O-\underset{\|}{C}-O}{\underset{(CH)_m}{\|}}\begin{array}{c}R^4\\R^3\end{array}$ $R^5$ | $R^6$ | n | Az | Melting point (°C.) |
|---|---|---|---|---|---|
| 59 | " | phenyl | 1 | imidazol-1-yl | 102–4° C. |
| 60 | 2,2-dimethyl-4-propyl-1,3-dioxolane | 4-methoxy-3-methylphenyl | 1 | 1,2,4-triazol-1-yl | $n_D^{20} = 1.5419$ |
| 61 | 2,2-dimethyl-4-ethyl-1,3-dioxolane | 4-bromo-2-methoxy-5-methylphenyl | 1 | " | $n_D^{20} = 1.5080$ |
| 62 | " | 4-bromo-6-ethyl-2-methoxyphenyl | 1 | " | $n_D^{20} = 1.5252$ |
| 63 | " | 4-methoxy-2,3-dimethylphenyl | 1 | " | $n_D^{20} = 1.5368$ |
| 64 | " | 4-chlorophenyl | 1 | 1,2,4-triazol-1-yl | 138° C. |
| 65 | " | phenyl | 1 | " | 97° C. |
| 66 | " | 4-chlorophenyl | 1 | imidazol-1-yl | 137° C. |
| 67 | " | 4-chlorophenoxy | 1 | imidazol-1-yl | viscous oil |
| 68 | 2,2-dimethyl-4-propyl-1,3-dioxolane | " | 1 | " | 153–54 (× HCl) |

-continued

| Example No. | R⁵ (structure) | R⁶ | n | Az | Melting point (°C.) |
|---|---|---|---|---|---|
| 69 | 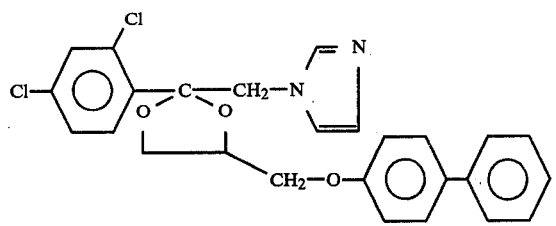 | " | 1 | " | viscous oil |
| 70 | 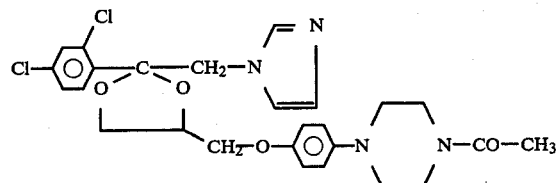 | 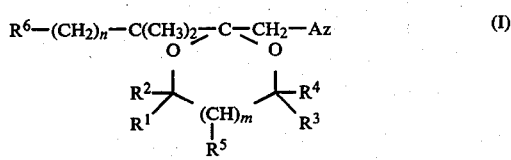 | 1 | " | $n_D^{20} =$ 1,5043 |

NDS* = 1,5-naphthalenedisulphonic acid

The following Example illustrates the in vitro antimycotic activity of the compounds used in the compositions of the present invention.

The compounds indicated below were employed as comparison substances in the Example which follows:

(A)

4-(4-biphenylyloxymethyl)-2-(2,4-dichlorophenyl)-2-(imidazol-1-yl-methyl)-1,3-dioxolane (B)

4-[4-(4'-acetylpiperazin-1-yl)-phenoxymethyl]-2-(2,4-dichlorophenyl)-2-(imidazol-1-yl-methyl)-1,3-dioxolane

EXAMPLE A

Antimycotic in vitro activity

Description of the experiment:

The in vitro tests were carried out in a series dilution test with germ inocula of an average of $5 \times 10^4$ germs/ml of substrate. The nutrient medium was (a) for dermatophytes and moulds: Sabouraud's milieu d'epreuve and (b) for yeasts: meat extract/glucose broth.

The incubation temperature was 20° C. and the duration of incubation was 24 to 96 hours in the case of yeasts and 96 hours in the case of dermatophytes and moulds.

In this test, the compounds of the Examples 1, 2, 12, 13, 14 and 25, in particular, exhibit a better antimycotic action than the compounds (A) and (B) known from the state of the art.

What is claimed is:

1. A pharmaceutical composition containing as an active ingredient an antimycotically effective amount of a compound which is a 2-azolymethyl-1,3-dioxolane or -dioxane derivative of the formula $$R^6-(CH_2)_n-C(CH_3)_2-C-CH_2-Az \quad (I)$$

or a pharmaceutically acceptable acid addition salt thereof, in which

Az represents imidazol-1-yl,

R¹, R² and R³ independently represent a hydrogen atom, or a straight-chain and branched alkyl group having 1 to 4 carbon atoms;

R⁴ represents a hydrogen atom, a straight-chain or branched alkyl group which has 1 to 4 carbon atoms and which is optionally substituted by hydroxyl, alkoxy having 1 to 4 carbon atoms, dialkylamino and dialkylaminocarbonyl, each having 1 or 2 carbon atoms in each alkyl part, optionally substituted phenoxy and optionally substituted phenylalkoxy having 1 to 4 carbon atoms in the alkyl part, optionally substituted phenylcarboxy and optionally substituted phenylalkylcarboxy having 1 to 4 carbon atoms in the alkyl part, alkylsulphonyloxy having 1 to 4 carbon atoms and optionally substituted phenylsulphonyloxy, or R⁴ represents an optionally substituted phenyl radical or an optionally substituted phenylalkyl radical having 1 to 4 carbon atoms in the alkyl part; or R¹ and R³ additionally together represent a tetra- or pentamethylene bridge which is optionally substituted by alkyl having 1 to 4 carbon atoms;

$R^5$ represents a hydrogen atom or a straight-chain and branched alkyl group having 1 to 4 carbon atoms; m is 0 or 1;

$R^6$ represents a hydrogen or halogen atom, a cyano radical, straight-chain or branched alkyl having 1 to 4 carbon atoms, optionally substituted phenyl, or a grouping of the formula —X—$R^7$, —COO$R^8$ or —CONH$R^9$, in which X represents an oxygen or sulphur atom or an SO- or SO$_2$ group, $R^7$ represents straight-chain or branched alkyl having 1 to 4 carbon atoms, halogenoalkyl having 1 or 2 carbon atoms and 1 to 5 identical or different halogen atoms, cyano, optionally substituted phenyl or optionally substituted phenylalkyl having 1 to 4 carbon atoms in the alkyl part;

$R^8$ represents straight-chain or branched alkyl having 1 to 4 carbon atoms;

$R^9$ represents straight-chain or branched alkyl having 1 to 4 carbon atoms or optionally substituted phenyl and in which the phenyl part of the substituents on the alkyl group of $R^4$, or the phenyl or phenylalkyl group of $R^4$, and/or of $R^7$ and/or the phenyl radical of $R^6$ and/or $R^9$ is, or are, substituted by substituent(s) selected from halogen, alkyl having 1 to 4 carbon atoms, alkoxy and alkylthio, each having 1 or 2 carbon atoms, halogenalkyl, halogenalkoxy and halogenoalkylthio, each having 1 to 2 carbon atoms and 1 to 5 identical or different halogen atoms, dimethylamino, acetylamino, acetylmethylamino, and piperazine which is optionally substituted by methyl or acetyl, and n is 0 or 1 in admixture with a solid or liquid gaseous diluent, or in admixture with a liquid diluent other than a solvent of a molecular weight less than 200 except in the presence of a surface active agent.

2. A composition according to claim 1 in which the active ingredient is a compound, in which $R^1$, $R^2$ and $R^3$ individually have the same meaning as in claim 1;

$R^4$ represents a hydrogen atom, or a straight-chain or branched alkyl radical which has 1 to 4 carbon atoms and which is optionally substituted by hydroxyl, methoxy, ethoxy, dimethylamino, dimethylaminocarbonyl, optionally substituted phenoxy and benzyloxy, methylcarboxy, ethylcarboxy, optionally substituted phenylcarboxy and benzylcarboxy, methylsulphonyloxy, ethylsulphonyloxy or optionally substituted phenylsulphonyloxy, or $R^4$ represents an optionally substituted phenyl radical or an optionally substituted benzyl radical;

$R^1$ and $R^3$ additionally together can represent a tetramethylene bridge;

$R^5$ represents a hydrogen atom or a methyl or ethyl group;

$R^6$ represents a hydrogen, fluorine, chlorine or bromine atom, a methyl, ethyl, propyl or optionally substituted phenyl radical, or a grouping of the general formula —X—$R^7$, —COO$R^8$ or —CONH$R^9$, in which $R^7$ represents a methyl, ethyl, trifluoromethyl or cyano radical or an optionally substituted phenyl or benzyl radical;

$R^8$ represents a methyl or ethyl radical;

$R^9$ represents a methyl, ethyl or optionally substituted phenyl radical, n is 1;

Az, X and m have the meaning given in claim 1 and in which optional substituents on $R^4$, $R^7$ and $R^9$ have the same meaning as in claim 1.

3. A composition according to claim 2, in which the phenyl part of the substituents on the alkyl group of $R^4$, or the phenyl or benzyl group of $R^4$ and/or $R^7$, and/or the phenyl radical of $R^6$ and/or $R^9$ is, or are substituted by a substituent selected from fluorine, chlorine, methyl, ethyl, methoxy, methylthio, trifluoromethyl and trifluoromethylthio, dimethylamino, acetylamino, acetyl-methyl-amino, and 4-acetyl-piperazin-1-yl, nitro, methylcarbonyloxy and ethylcarbonyloxy.

4. A composition according to claim 3 in which the phenyl-substituents are selected from those stated in claim 5 with the exception of nitro, methylcarbonyloxy and ethylcarbonyloxy.

5. A composition according to claim 1 in which the active ingredient is the compound of the formula

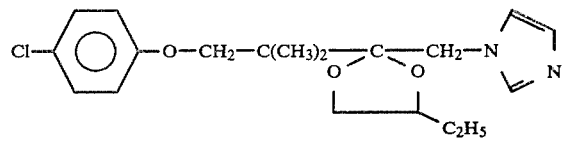

or a pharmaceutically acceptable acid-addition salt thereof.

6. A composition according to claim 1 in which the active ingredient is the compound of the formula

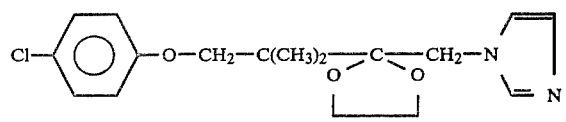

or a pharmaceutically acceptable acid-addition salt thereof.

7. A composition according to claim 1 in which the active ingredient is the compound of the formula

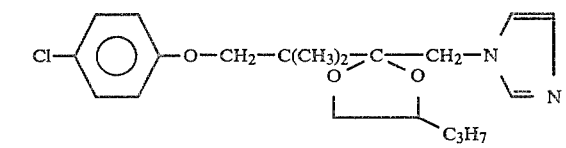

or a pharmaceutically acceptable acid-addition salt thereof.

8. A composition according to claim 1 in which the active ingredient is the compound of the formula

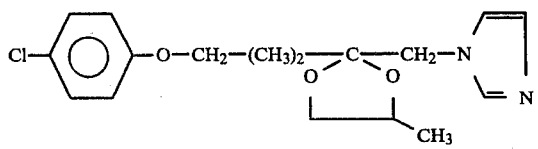

or a pharmaceutically acceptable acid-addition salt thereof.

9. A composition according to claim 1 in which the active ingredient is the compound of the formula

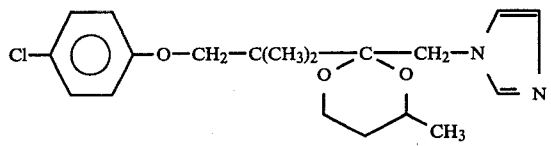

or a pharmaceutically acceptable acid-addition salt thereof.

10. A pharmaceutical composition of claim 1 in the form of a sterile aqueous solution.

11. A pharmaceutical composition of claim 1 in the form of a physiologically isotonic aqueous solution.

12. A composition according to claim 1, containing from 0.5 to 95% by weight of the said active ingredient.

13. A medicament in dosage unit form comprising an antimycotically effective amount of a compound as defined in claim 1 and an inert pharmaceutical carrier.

14. A medicament of claim 13 in the form of tablets, pills, dragees, capsules, ampoules, or suppositories.

15. A method of combating mycoses in warm-blooded animals which comprises administering to the animals an antimycotically effective amount of a composition as defined in claim 1.

16. A method according to claim 15 in which the active compound is administered in an amount of 10 to 300 mg per kg body weight per day.

17. A method according to claim 15 or 16 in which the active compound is administered parenterally.

* * * * *

UNITED STATES PATENT AND TRADEMARK OFFICE
CERTIFICATE OF CORRECTION

PATENT NO. : 4,470,994

DATED : September 11, 1984

INVENTOR(S) : Wolfgang Krämer, et al

It is certified that error appears in the above-identified patent and that said Letters Patent is hereby corrected as shown below:

| | |
|---|---|
| Col. 1, line 45, Col. 3, line 28, Col. 4, line 10, Col. 4, line 26, Col. 4, line 61 | Delete "m" and substitute --$\underline{m}$-- |
| Col. 1, line 61, Col. 3, line 27, Col. 4, line 9, Col. 4, line 26, Col. 4, line 51 | Delete "n" and substitute --$\underline{n}$-- |
| Col. 4, line 24 | Delete rightside of formula and substitute -- 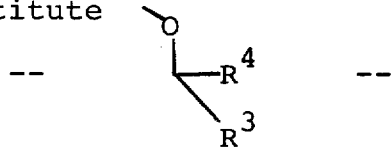 -- |
| Col. 18, Example 38, under column "AZ" | Delete formula and substitute --  -- |
| Col. 27, line 33 | After "1" first instance, delete "to" and substitute --or-- |

UNITED STATES PATENT AND TRADEMARK OFFICE
CERTIFICATE OF CORRECTION

PATENT NO. : 4,470,994

DATED : September 11, 1984

INVENTOR(S) : Wolfgang Krämer, et al

It is certified that error appears in the above-identified patent and that said Letters Patent is hereby corrected as shown below:

Col. 28, line 26        After "claim" delete "5" and substitute --3--

Signed and Sealed this

Twenty-third Day of April 1985

[SEAL]

Attest:

DONALD J. QUIGG

Attesting Officer      Acting Commissioner of Patents and Trademarks